United States Patent [19]

Muramoto et al.

[11] 3,980,463

[45] Sept. 14, 1976

[54] PROCESS FOR PRODUCING GRANULAR COMPOSITION FOR USE IN AGRICULTURE AND HORTICULTURE

[75] Inventors: Noboru Muramoto, Ikeda; Yukikazu Okamoto, Toyonaka; Kazuo Kamaya, Minoo; Kunihiro Kawaji, Hirakata; Makoto Shiraki, Ibaragi, all of Japan

[73] Assignee: Sumitomo Chemical Company, Limited, Osaka, Japan

[22] Filed: Oct. 16, 1974

[21] Appl. No.: 515,377

Related U.S. Application Data

[63] Continuation-in-part of Ser. No. 199,336, Nov. 16, 1971, abandoned.

[30] Foreign Application Priority Data

Nov. 16, 1970  Japan............................. 45-101344

[52] U.S. Cl. ........................................ 71/86; 71/65; 71/79; 71/87; 71/92; 71/95; 71/106; 71/117; 71/DIG. 1; 424/224; 424/274; 424/300; 424/317; 424/14

[51] Int. Cl.² ...................... A01N 9/36; A01N 9/00; A01N 17/00; A01N 17/08

[58] Field of Search.................. 71/79, DIG. 1, 117, 71/86; 424/14

[56] References Cited
UNITED STATES PATENTS

| | | | |
|---|---|---|---|
| 2,992,090 | 7/1961 | Littler | 71/120 |
| 3,137,618 | 6/1964 | Pearce | 71/DIG. 1 |
| 3,149,953 | 9/1964 | Miller | 71/DIG. 1 |
| 3,168,437 | 2/1965 | Galloway | 71/DIG. 1 |
| 3,657,446 | 4/1972 | Blockmare | 71/79 X |
| 3,705,019 | 12/1972 | Mesiah | 71/93 |
| 3,748,277 | 7/1973 | Wagner | 71/DIG. 1 |

OTHER PUBLICATIONS

Granulation and Apparatus Therefor, Japanese Mechanical Association, p. 6, 1967.

Konac et al., Food Engineering, Aug. 1962, pp. 41-44.

*Primary Examiner*—Joseph Paul Brust
*Attorney, Agent, or Firm*—Sughrue, Rothwell, Mion, Zinn and Macpeak

[57] ABSTRACT

A granular composition for use in the agricultural and horticulture fields is prepared by mixing an active ingredient, such as an insecticide, fungicide or herbicide and a solvent or a binder with a carrier consisting of 0–30% of particles larger than 149 $\mu$ (100 mesh), 40–90% of particles between 149 $\mu$ (100 mesh) and 46 $\mu$ (300 mesh) and 10–30% of particles smaller than 46 $\mu$. Finely divided particles of moisture-absorbing substances may be added when the carrier has been moderately granulated in the course of the production process. The composition is suited for spraying by helicopters or multi-nozzle hoses on dusters, for example.

7 Claims, No Drawings

3,980,463

PROCESS FOR PRODUCING GRANULAR COMPOSITION FOR USE IN AGRICULTURE AND HORTICULTURE

CROSS-REFERENCE TO RELATED APPLICATION

This application is a continuation-in-part of copending application Ser. No. 199,336, filed Nov. 16, 1971, of Noboru Muramoto et al., entitled PROCESS FOR PRODUCING GRANULAR COMPOSITION FOR USE IN AGRICULTURE AND HORTICULTURE, now abandoned.

BACKGROUND OF THE INVENTION

1. Field of the Invention

This invention relates to an agricultural and horticultural granular composition comprising a major proportion of particles having a size of from 105 $\mu$ (150 mesh) to 297 $\mu$ (48 mesh), "mesh" being according to the Tayer Standard Screen Sieves.

2. Description of the Prior Art

In recent years, the spraying of agricultural chemicals in the form of dusts or granules by means of helicopters or multi-nozzle hose dusters has been practiced in order to save labor in the spraying operation. Since the dusts or granules have various defects which make them unsuitable for spraying by such methods, particles having an intermediate size between a dust and a granule, i.e. a size of 105 $\mu$ (150 mesh) to 297 $\mu$ (48 mesh), have come forth as promising formulations of agricultural chemicals from the standpoint of effect and prevention of public hazards. Compositions having such a size distribution are prepared either by coating an agricultural chemical and a suitable assistant on to the surface of the carrier particles, which have been previously sifted to the desired size, or by absorbing them into a granular carrier. These formulating methods involve simple process steps, but still have many defects. According to these methods, carrier particles which have been sifted to the desired sizes of 48 to 150 mesh are used, and therefore, this imposes a limitation on the supply of carriers and constitutes a drawback against mass-production.

If a non-absorbing substance, such as calcium carbonate or silica is used as a carrier in the above-mentioned size range, the active ingredient does not penetrate into the carrier particles when applied by a coating method, and therefore, it is difficult to form a composition having an active ingredient concentration above certain level. In addition, as the coated portion has a high concentration of the active ingredient, it has the defect of causing phytotoxicity or posing toxicity problems for humans because the coated portion may be stripped off and become powdered by direct contact with the human body or during transportation or spraying.

On the other hand, absorbing granular carriers usually have a high surface activity, and may be easily decomposed, depending upon the properties of the active ingredient. Furthermore, since the active ingredient is strongly adhered to the inner part of such carrier particles, the release of the active ingredient is slow and incomplete, therefore the effect is not sufficient.

SUMMARY OF THE INVENTION

It has now been found that if a carrier having a specific size distribution is used and mixed with a liquid, granulation occurs and the carrier particles have the properties of automatically attaining the desired particle size range.

According to the present invention, there is provided a process for producing an agricultural and horticultural granular composition comprising a major proportion of particles having a size of from 105 $\mu$ (150 mesh) to 297 $\mu$ (48 mesh), which comprises mixing an active ingredient and a solvent and/or a binder with a carrier consisting of 0 to 30% of particles larger than 149 $\mu$ (100 mesh), 40 to 90% of particles of a size between 149 $\mu$ (100 mesh) and 46 $\mu$ (300 mesh), and 10 to 30% of particles smaller than 46 $\mu$ (300 mesh).

The critical feature of the present invention resides in the use of a carrier having the specific particle size distribution described above which leads to a granular composition having at least 80% of particles having a size of from 150 to 48 mesh, which size range is stipulated in the agricultural chemical industry.

Accordingly, it is an object of the present invention to provide an economical process for producing an agricultural and horticultural granular composition very easily and efficiently.

DETAILED DESCRIPTION OF THE INVENTION

According to the process of the present invention, a carrier consisting of 0 to 30% of particles having a size larger than 149 $\mu$ (100 mesh), 40 to 90% of particles having a size of 149 $\mu$ (100 mesh) to 46 $\mu$ (300 mesh), and 10 to 30% of particles having a size smaller than 46 $\mu$ (300 mesh) is put in a stirring-type mixer known in the art, such as ribbon mixer or Nauta mixer, followed by addition of an active ingredient and a solvent and/or a binder. Any significant amount of particles larger than 48 mesh should be avoided, and preferably all particles will be smaller than 48 mesh. These materials are mixed with each other for 10 to 30 minutes, whereby the active ingredient and the binder are uniformly mixed and the carrier particles are granulated to moderate size.

So long as the carrier has the size distribution defined in the present invention, the carrier particles are not enlarged more than necessary. When these materials have been moderately mixed and granulated, moisture-absorbing finely divided powders such as kaolinite-type clay, white carbon, diatomaceous earth, or other foamed mineral substances having a size smaller than 46 $\mu$ (300 mesh) may be added, and the mixing continued for an additional 5 to 10 minutes. This results in coating of the absorbing finely divided powders on to the surfaces of the wet granulated particles, and the particles somewhat increase in flowability and become dry. Therefore, the granulated particles do not form masses by adhering to one another.

When the resultant granular composition is dried by a suitable method such as by fluidized bed type drying, vibration drying or flush drying, particles having the desired size for preferred granular compositions can be obtained at a yield of 80 to 95%. The resultant granular composition contains particles having a size smaller than 105 $\mu$ particles have a size larger than 63 $\mu$ (250 mesh).

Of those particles which have a particle size larger than 297 $\mu$ (48 mesh), the percentage of particles smaller than 500 $\mu$ (32 mesh) is generally about 5 to 8%, and these particles may safely be present in the resulting granular composition. Hence, it is sufficient that sifting after drying is performed only for removing particles larger than 500 $\mu$ (32 mesh). Particles having a size greater than 500 μ (32 mesh) are formed usually in an amount of 5%. But if they are recycled to the mixing step in the presence of moisture, they again absorb water and are disintegrated, with the result that together with a fresh supply of the carrier, they are granulated to particles of appropriate sizes. Such particles may alternatively be pulverized by a suitable pulverizer, and the particles adjusted to proper sizes. Therefore, there is hardly any loss of material in the process of the present invention and the efficiency of material use is almost 100%.

Since the granular composition of the present invention is substantially free of fine powders smaller than 105 μ (150 mesh), no accidents ascribable to powder scattering occurs at the time of spraying. Furthermore, the granular composition obtained consists of almost spherical particles, has good flowability and possesses moderate hardness. By reason of these properties, the granular composition obtained by the process of the present invention gives off almost no fine powders due to breakage during transportation or spraying, and therefore hazards resulting therefrom are greatly reduced.

The amount of water to be added during the manufacture of the granular composition according to the present invention may be 1 to 10%, preferably 2 to 6%, namely, as low as ⅓ to 1/5 of that needed in the ordinary production of granular composition. Thus, it is sufficient if the drying of the resulting composition is performed only to a slight extent, and drying does not require high temperature conditions. This naturally leads to a drastic reduction in the decomposition and volatilization of active ingredients during the drying step. In addition, the major portion of the manufacturing process comprises the mixing step which only requires a relatively short period of time, with a subsequent very simple drying step. Accordingly, agricultural and horticultural granular composition comprising a major proportion of particles of the specific size range given hereinabove can be produced by the process of the present invention very easily, efficiently and economically.

The process of the present invention basically differs from known mix-granulating methods using blender granulators, bin granulators, or turbulizers in the following ways.

Firstly, the process of the present invention does not require a special mixing machine as described above.

Secondly, these conventional methods employ carriers in the form of fine powders. It is generally recognized that the finer particle size of a powder, the better the granulating properties and the properties of the resulting granulated composition become. The present invention, however, requires the use of carriers having the specific size distribution heretofore described.

Thirdly, with these conventional methods fine liquid droplets are added as nuclei, and powders are deposited thereon to form granules. In contrast, in the present invention, no special care need be exercised in adding the liquid. Even if the liquid is added in one large portion, it is fully distributed by mixing to ensure moderated granulation.

Lastly, the formation of large particles cannot be avoided with the conventional methods. Moreover, the particles are non-uniform, and the yield of those particles which have the desired size range is very small. According to the present invention, the formation of large particles can be inhibited by using carriers of the specific particle size distribution described hereinabove. Particles having the desired size range can be produced in good yields.

The granulated mechanism according to the process of the invention is not entirely clear. It is assumed however that the use of the carrier of the specific particle size distribution brings about a granulating action of aggregating fine particles and at the same time, depending upon large particles in the carrier, a disintegrating action which prevents size enlargement of large particles and therefore the formation of large particles is inhibited and the size range of the resultant granular composition becomes limited. It is furthermore believed that fine particles intrude into interstices among large particles to form a firmer granular composition, and that the resulting wet granules are prevented from sticking to one another to form large particles by adding the moisture-absorbing fine powders.

The particle size distribution of carriers used in the present invention is actually within the range of particle size distributions of particles obtained by pulverizing rock for mineral carriers by ordinary rough pulverization, and is not a special one. For practical purposes, intermediate products before sifting of carriers for dust formulations are used. Hence, such carriers can be prepared in quantities more efficiently and economically than in the case of preparing finer or larger particles.

Any carriers having the specific size distribution heretofore described can be used in the present invention, which include not only those frequently used mineral carriers, but also fertilizers, organic salts, inorganic salts, and the like. Specific examples are roughly pulverized products of kaolinite-type clay, talc, bentonite, perlite, pumice, silica rock, and calcium carbonate, various fertilizers, shell powder, leaf powder, stalk powder, wood powder, crystalline saccharide, synthetic powder such as polyvinyl chloride, polystylol, polyethylene powder, anhydrous sodium sulfate, salt, and mixtures of these. It will thus be clear to one skilled in the art that any carrier as this term is understood in the agricultural/horticultural field may be used in the present invention. However, in all events, the size distribution must reside within the scope of the present invention.

Insecticides, fungicides and herbicides can both be used as the active ingredient. Whether the active ingredient is liquid or crystalline, the granulation according to the invention can be performed. If the active ingredient is liquid, it is mixed with the carrier either directly or after dissolving or dispersing it in a solvent or a solution of a binder. If it is crystalline, it is mixed with the carrier after grinding to proper sizes or after dissolving or dispersing in a solvent or a solution of a binder. If it is crystalline, it is used after dissolving or dispersing in a solvent or a solution of a binder, but if it is not soluble it is mixed with the carrier after grinding to proper sizes falling into the scope of the present granular composition.

The solvent must generally have the following properties:

1. It should not react with the active ingredient, i.e., organic bases and organic acids thus usually cannot be employed.

2. Usually solvents with an extremely high volatility or high boiling point (above 150°C) are not used.

As the solvent to be used in the present invention, water is most preferred, but other solvents can also be used. Examples of the solvents include alcohols, ketones, petroleum, aromatic and halogenated hydrocarbons. The amount of the solvent is 1–10 wt.%, preferably 2 to 6% by weight, based on the total weight of the composition.

The binders that are useful in the present invention include water soluble or organic solvent-soluble compounds. Examples of the water-soluble binders are lignin sulfonates, carboxymethyl cellulose, polyvinyl alcohol, starch, sodium alginate, and acrylic resins. Such a binder may be added as an aqueous solution, or added in the form of powders to carrier followed by addition of water. Examples of binder soluble in organic solvents include rosin, coumarone resin, petroleum resin, shellac, and gelatin. These are used in the same way as in the case of the water-soluble binders. Generally, the use of water-soluble binders gives rapid releasing granular compositions, and the use of organic solvent soluble binders leads to slow-releasing compositions. Well-known high molecular weight adhesive agents, such as EVA(ethylene vinylacetate copolymer) emulsions, VA(vinylacetate) emulsions etc. may also be employed. The binders are used by being dissolved in a desired solvent selected according to the materials involved, and a rapid dissolving speed is required. Therefore, a find binder particle size is preferable. However, the binder particle size has no relation with the point of the present invention.

The carrier/binder/active ingredient ratio can be freely varied if each component is included within the scope of the size according to the present invention. From the practical standpoint, it is preferred that the binder content is 0.5–5% (by weight) and the active ingredient content is 3–5% (by weight). The active ingredient may be contained up to about 30% (by weight). Thus, it can be seen that the critical feature of the present invention is the size distribution, and the ratios of the components can be freely varied so long as an effective amount of the active ingredient is bound to the carrier. One skilled in the art will be able to select the exact ratios used depending upon the desired end use of the product.

The invention will be further illustrated by the following Examples, which demonstrate that when a carrier having a particle size distribution outside the range specified in the present invention is used, the yield of particles of the desired size range is reduced.

EXAMPLE 1

Granular compositions were prepared using O,O-dimethyl-0-3-methyl-4-nitrophenyl phosphorothioate (Sumithion, registered trademark of Sumitomo Chemical Co., Ltd.) as an active ingredient and either kaolinite-type clay or calcium carbonate of various size distributions (Run No. 1 is an example of the present invention, and other Runs are controls).

1. Preparation Procedure

The carrier (13.455 kg) and 750 g of calcium ligninsulfonate as a binder were put into a 30-liter Nauta mixer, and with stirring, 495 g of Sumithion was poured into it. The mixing was performed for about 10 minutes, and when the Sumithion was uniformly mixed, 450 ml. of water was added. The mixing was continued for about 20 minutes to dissolve the calcium ligninsulfonate fully, and the size of the carrier was moderately adjusted. With continued mixing, 300 g of white carbon (fine powders of hydrous silicic acid) was put into the mixer, and mixed for about 5 minutes with the resultant mixture to complete the size adjustment. The resulting granular composition was dried in a fluidized bed type dryer. (Speed Dryer, product of Fuji Seisakusho) using warm air at 60°C., and sifted using a 32-mesh wire gauze.

2. Size distribution of the carrier, and the size distribution of the product together, with the yield of granular composition having a size smaller than 32 mesh a. Size distribution of the carrier:

| Kaolinite-type clay | | | |
| --- | --- | --- | --- |
| Particle size (mesh) | Smaller than 300 mesh (%) | 300 to 100 mesh (%) | Larger than 100 mesh (%) |
| Run Nos. | | | |
| 1 | 15.8 | 71.1 | 13.1 |
| 2 | 15.3 | 42.1 | 42.6 |
| 3 | 37.8 | 43.7 | 18.5 |
| 4 | 65.3 | 31.8 | 2.9 |
| 5 | 99.7 | 0.3 | 0 |
| 6 | 5.5 | 80.0 | 14.5 |
| Calcium Carbonate | | | |
| Particle size (mesh) | Smaller than 300 mesh (%) | 300 to 100 mesh (%) | Larger than 100 mesh (%) |
| Run Nos. | | | |
| 1 | 22.6 | 69.1 | 8.3 |
| 2 | 49.3 | 47.1 | 3.6 |
| 3 | 13.6 | 41.7 | 44.7 |
| 4 | 99.3 | 0.7 | 0 | b. Size distribution of the resulting compositions and yield of granular composition having a size smaller than 32 mesh:

| Kaolinite-type clay | | | |
| --- | --- | --- | --- |
| Particle size (mesh) | Smaller than 150 mesh (%) | 48 to 150 mesh (%) | 32 to 48 mesh (%) | Yield of granular composition smaller than 32 mesh (%) |
| Run Nos. | | | | |
| 1 | 7.9 | 86.3 | 5.8 | 94.6 |
| 2 | 17.4 | 57.3 | 25.3 | 72.1 |
| 3 | 20.2 | 49.6 | 30.2 | 74.6 |
| 4 | 35.7 | 34.5 | 29.8 | 55.7 |
| 5 | 14.1 | 29.5 | 56.4 | 31.9 |
| 6 | 11.6 | 53.3 | 35.1 | 68.5 |
| Calcium Carbonate | | | | |
| Particle size (mesh) | Smaller than 150 mesh (%) | 48 to 150 mesh (%) | 32 to 48 mesh (%) | Yield of granular composition smaller than 32 mesh (%) |

-continued

| Run Nos. | | | | |
|---|---|---|---|---|
| 1 | 3.4 | 90.4 | 6.2 | 95.4 |
| 2 | 23.5 | 52.8 | 23.7 | 67.5 |
| 3 | 18.3 | 51.0 | 30.7 | 70.1 |
| 4 | 12.5 | 36.2 | 51.3 | 34.8 |

It will be clear from the foregoing results that if the particle size of the carrier used is appropriate, the yield is high, and compositions having the specific particle size distribution described hereinabove can be obtained.

If the particle size of the carrier is outside the range specified in the present invention, some amount of particles within the 48–150 mesh range can be obtained, but particles having a size smaller than 150 mesh and between 32 and 48 mesh increase. Hence, a two stage sifting at 150 mesh and 48 mesh must be performed, and the yield becomes smaller. Such is not commercially feasible.

EXAMPLE 2

Granular compositions were prepared in the same way as set forth in Example 1 using a 1000-liter Nauta mixer and kaolinite-type clay and calcium carbonate of the specific size distributions.

1. Preparation procedure

The carrier (897 Kg) and 50 Kg of calcium lignin-sulfonate were put into the mixer, and with stirring, 33 Kg of Sumithion was poured into it. The mixing was performed for 10 minutes, and 30 liters of water was added. The mixing was continued for an additional 20 minutes, and 20 Kg of white carbon was further added. Mixing was then continued for 5 minutes. The product was withdrawn and dried in a band-type dryer with warm air at 60°C., followed by sifting with a 32-mesh wire gauze:

2. Particle size distribution of the carriers and the size distribution of the resulting compositions together with the yield of the granular composition smaller than 32 mesh a. Particle size distribution of the carrier:

| Carriers | Smaller than 300 mesh (%) | 300 to 100 mesh (%) | larger than 100 mesh (%) |
|---|---|---|---|
| Clay | 16.2 | 70.8 | 13.0 |
| Calcium carbonate | 22.2 | 67.3 | 10.5 | b. Particle size distribution of the resulting composition and the yield of granular composition smaller than 32 mesh:

| Carriers | Smaller than 150 mesh (%) | 150 to 48 mesh (%) | 48 to 32 mesh (%) | Yield of granular composition smaller than 32 mesh (%) |
|---|---|---|---|---|
| Clay | 3.8 | 89.2 | 7.0 | 91.5 |
| Calcium carbonate | 5.2 | 91.5 | 3.3 | 93.6 |

It was observed that on plant scale processing, particles of the size distribution of the granular composition of the invention can be obtained in good yields.

EXAMPLE 3

A ribbon mixer was charged with 9.07 Kg of kaolinite-type clay having the size distribution shown below and 500 g of calcium lignin-sulfonate and 330 g of 2-secondary butyl phenyl-N-methylcarbamate was added with stirring. The mixing was performed for about 10 minutes, and 300 ml. of water was added. The mixing was performed for approximately an additional 10 minutes to granulate these materials moderately. Then, 100 g of finely divided powders of diatomaceous earth was added, and the mixing was continued for 5 minutes. The resulting granular composition was withdrawn and dried in a fluidized bed dryer with warm air at 50°C. The size distributions of the carrier and the resulting composition are shown below.

1. Particle size distribution of the carrier

| Smaller than 300 mesh | 300–100 mesh | Larger than 100 mesh |
|---|---|---|
| 19.1% | 66.9% | 14.0% |

2. Size distribution of the resulting composition and the yield of granular composition than 32 mesh

| Smaller than 150 mesh | 150–48 mesh | 48–32 mesh | Yield |
|---|---|---|---|
| 7.7% | 83.7% | 8.6% | 89.6% |

EXAMPLE 4

A 30-liter Nauta mixer was charged with 17.94 Kg of clay having the size distribution indicated below, 1.0 Kg of calcium lignin-sulfonate, and 660 g of 3,4-dimethylphenyl-N-methylcarbamate (Meobal, registered trademark of Sumitomo Chemical Co., Ltd.) ground to a size below about 200 mesh, and these materials were uniformly mixed. Thereafter, 800 ml. of water was added, and the mixing was performed for about 20 minutes to granulate the carrier moderately. Fine powders of kaolinite-type clay (400 g) were added, and the granulation was completed. The granulated composition with withdrawn, and dried in a fluidized bed type dryer with warm air at 50°C to form 18.1 Kg of a granulated composition containing Meobal in concentration of 3%. The particle size distribution of the carrier and the size distribution of the composition together with the yield of particles smaller than 32 mesh is shown below.

1. Particle size distribution of the carrier

| Smaller than 300 mesh | 300–100 mesh | Larger than 100 mesh |
| --- | --- | --- |
| 20.0% | 63.4% | 16.6% |

2. Size distribution of the resulting composition and the yield of granular composition smaller than 32 mesh

| Smaller than 150 mesh | 150–48 mesh | 48–32 mesh | Yield |
| --- | --- | --- | --- |
| 6.0% | 85.6% | 8.4% | 90.5% |

EXAMPLE 5

A 30-liter Nauta mixer was charged with 17.50 Kg of the same carrier as used in Example 4, 1.0 Kg of calcium lignin-sulfonate, and 440 g of pulverized product of Meobal, and these materials were mixed. Then, 660 g of Sumithion was added, and the mixing was performed for 10 minutes. Then, 600 ml. of water was added, and the mixing was continued further for 20 minutes. Finally, 400 g of fine powders of perlite was added, and the mixing was continued for 5 minutes. The resulting composition was dried and sifted as in Example 4 to form 17.66 Kg of a granular composition containing 3% Sumithion and 2% Meobal.

The size distribution of the resulting composition and the yield of granular composition smaller than 32 mesh are given below.

| Smaller than 150 mesh | 150–48 mesh | 48–32 mesh | Yield |
| --- | --- | --- | --- |
| 2.4% | 91.1% | 6.5% | 88.3% |

EXAMPLE 6

A 10-liter kneader was charged with 8.98 Kg of calcium carbonate having the size distribution indicated below, 440 g of O,O-diethyl-O-(02-isopropyl-4-methyl-6-pyrimidinyl) phosphorothioate (Diazinon, trademark of Geigy, Switzerland), and a solution of 80 g of polyvinyl alcohol (degree of polymerization: 500) in 400 cc of water, and these materials were mixed for 10 minutes to granulate the carrier moderately. Then, 500 g of kaolinite-type clay was added and mixing was performed for an additional 10 minutes. The resulting composition was dried in a fluidized bed type dryer with warm air at 40°C and sifted with a 32-mesh wire gauze to form 9.25 Kg of a granular composition containing 4% of Diazinon. The particle size distribution of the carrier, and the particle size distribution of the resulting composition together with the yield of particles smaller than 32 mesh are shown below.

1. Size distribution of the carrier

| Smaller than 300 mesh | 300–100 mesh | Larger than 100 mesh |
| --- | --- | --- |
| 18.9% | 60.1% | 21.0% |

2. Size distribution of the composition obtained and the yield of granular composition having a size smaller than 32 mesh

| Smaller than 150 mesh | 150–48 mesh | 48–32 mesh | Yield |
| --- | --- | --- | --- |
| 6.4% | 89.1% | 4.5% | 92.5% |

EXAMPLE 7

A 30-liter Nauta mixer was charged with 26.91 Kg of calcium carbonate, and a mixed solution of 300 g of shellac, 600 g of methanol, and 990 g of O,O-dimethyl-S-(N-methylcarbamoyl methyl) phosphorodithioate (Dimethaate) was added with stirring. Mixing was performed for 20 minutes to granulate the carrier moderately. Then, 1.8 Kg of diatomaceous earth was added, and mixing was continued to (for 5 minutes) complete the granulation. The resulting composition was withdrawn, dried in a vapor heating type fluidized bed dryer with warm air at 50°C, and sifted with a 32-mesh wire gauze to form 27.5 Kg of a granular composition containing 3% of Dimethoate. The size distribution of the carrier and the size distribution of the resulting composition together with the yield of particles smaller than 32 mesh are shown below.

1. Size distribution of the carrier

| Smaller than 300 mesh | 300–100 mesh | Larger than 100 mesh |
| --- | --- | --- |
| 11.0% | 70.5% | 18.5% |

2. Size distribution of the resulting composition and the yield of granular composition smaller than 32 mesh

| Smaller than 150 mesh | 150–48 mesh | 48–32 mesh | Yield |
| --- | --- | --- | --- |
| 3.8% | 90.5% | 5.7% | 91.7% |

EXAMPLE 8

A 30-liter Nauta mixer was charged with 9.07 Kg of kaolinite-type clay of the size distribution indicated below and 330 g of N-(3,5-dichlorophenyl) succinimide (Ohrie, registered trademark of Sumitomo Chemical Co., Ltd.), and these materials were mixed for about 10 minutes. Thereafter, 500 ml. of a 20% aqueous solution of polyvinyl alcohol was added with stirring, and mixing was performed for about 20 minutes to granulate the carrier moderately. Then, 500 g of fine powders of kaolinite-type clay was added, and the mixing was continued for about 10 minutes to complete the granulation. The resulting composition was taken out, dried in a fluidized bed type dryer with warm air at 50°C, and sifted with a 32-mesh sieve to form 8.41 Kg of a granular composition containing 3% of ohric.

The particle size distributions of the carrier and the resulting composition are shown below together with the yield of particles smaller than 32 mesh.

1. Size distribution of the carrier

| Smaller than 300 mesh | 300–100 mesh | Larger than 100 mesh |
|---|---|---|
| 24.7% | 66.8% | 8.5% |

2. Size distribution of the resulting composition and yield of granular composition smaller than 32 mesh

| Smaller than 150 mesh | 150–48 mesh | 48–32 mesh | Yield |
|---|---|---|---|
| 1.5% | 89.4% | 9.1% | 84.1% |

EXAMPLE 9

725 Kg of calcite having the size distribution indicated below, 50 Kg of calcium lignin-sulfonate and 220 Kg of 2,4-dichlorophenoxy acetic acid were put into a mixer and mixed for about 10 minutes. Thereafter, 65 liters of water were added, and mixing was continued for 20 minutes to complete the size adjustment. 5 Kg of fine powders of hydrous silicon hydroxide was then added, and the mixing was further continued for 5 minutes to complete the granulation. The resulting composition was taken out and dried in Band Type dryer with warm air at 60°C.

The particle size distribution of the carrier and the resulting composition are shown below together with the yield of particles smaller than 48 mesh.

1. Size distribution of the carrier

| Smaller than 300 mesh | 300–100 mesh | Larger than 100 mesh |
|---|---|---|
| 10.6% | 80.1% | 9.3% |

2. Size distribution of the resulting composition and yield of granular composition smaller than 48 mesh

| Smaller than 150 mesh | 150–48 mesh | Larger than 48 mesh | Yield |
|---|---|---|---|
| 2.1% | 94.1% | 3.8% | 96.2% |

The particles having a size smaller than 150 mesh, i.e., 2.1%, may safely be present in the resulting composition, and cutting only the particles having a size larger than 48 mesh, i.e., 3.8%, a granular composition containing 20% of 2,4-dichlorophenoxy acetic acid can be obtained at a yield of 96.2%.

Although the instant invention has been adequately described in the foregoing specification and Examples included therein, it is readily apparent that various changes and modifications can be made without departing from the spirit and scope thereof.

What we claim is:

1. A process for producing an agricultural or horticultural granular composition having at least 80% of particles having a size of from 105 microns (150 mesh) to 297 microns (48 mesh) which comprises mixing an effective amount of an agricultural or horticultural active ingredient and 1 to 10% by weight based on the total weight of the composition of a liquid medium or a liquid medium and a binder soluble therein, with a carrier having the following particle size distribution:

less than 30% by weight of particles larger than 149 microns (100 mesh), but which wholly pass through a size of 297 microns (48 mesh); and 10 to 30% by weight of particles smaller than 46 microns (300 mesh);

the balance being of particles within the range of 149 microns (100 mesh) to 46 microns (300 mesh), using a stirring-type mixer for 10 to 30 minutes to make granules whereby the granulation is completed and then drying.

2. The process of claim 1 wherein the liquid medium is water.

3. The process of claim 2 wherein the active ingredient is selected from the group consisting of an insecticide, fungicide and herbicide.

4. The process of claim 2 wherein the amount of the water is 2 to 6%, by weight, based on the total weight of the composition.

5. The process of claim 2 wherein said binder is a member selected from the group consisting of a lignin-sulfonate, carboxymethyl cellulose, polyvinyl alcohol, starch, sodium alginate, an acrylic resin, rosin, a coumarone resin, a petroleum resin, shellac and gelatin and said binder is present in an amount of 0.5 to 5% by weight based on the total weight of the composition.

6. The process of claim 2 wherein the carrier is a mineral selected from the group consisting of kaolinite-type clay, talc, bentonite perlite, pumice, silica rock and mixtures thereof.

7. The process of claim 1 wherein said stirring-type mixer is a nauta mixer, a ribbon blender, or a kneader.

* * * * *